(12) United States Patent
Weber

(10) Patent No.: US 7,056,298 B1
(45) Date of Patent: Jun. 6, 2006

(54) THUMB BRACE

(75) Inventor: James J. Weber, Santa Barbara, CA (US)

(73) Assignee: Weber Orthopedic Inc., Santa Paula, CA (US)

(*) Notice: Subject to any disclaimer, the term of this patent is extended or adjusted under 35 U.S.C. 154(b) by 0 days.

(21) Appl. No.: 11/155,050

(22) Filed: Jun. 17, 2005

(51) Int. Cl.
*A61F 5/00* (2006.01)

(52) U.S. Cl. .................... 602/22; 2/16; 2/21
(58) Field of Classification Search ............ 602/20–21, 602/64; 2/16, 21, 159, 161.4
See application file for complete search history.

(56) References Cited

U.S. PATENT DOCUMENTS

| | | | |
|---|---|---|---|
| 5,779,657 A * | 7/1998 | Daneshvar | 602/60 |
| 6,893,410 B1 | 5/2005 | Hely | |
| 2003/0191421 A1* | 10/2003 | Weaver et al. | 602/22 |

* cited by examiner

*Primary Examiner*—Henry Bennett
(74) *Attorney, Agent, or Firm*—William W. Haefliger

(57) ABSTRACT

A thumb and wrist brace comprising, in combination, the brace having multiple elongated stiffeners with extents generally alongside the thumb, and strap means carried to wrap relative to the thumb and proximate the stiffener extents, whereby the main extent of the thumb is substantially immobilized by the stiffeners and strap means, at least one stiffener extending to a wrist zone of the brace.

26 Claims, 6 Drawing Sheets

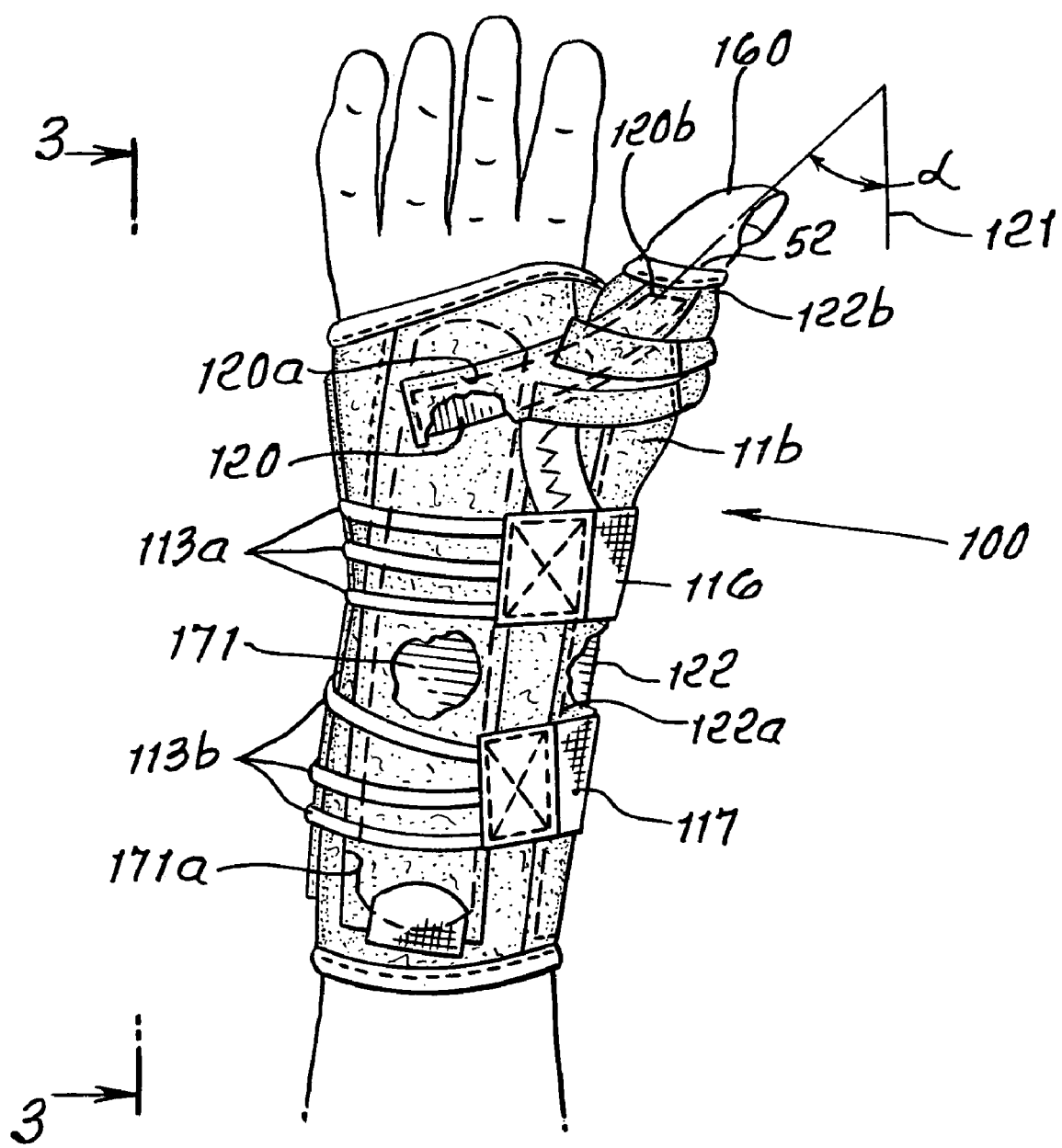

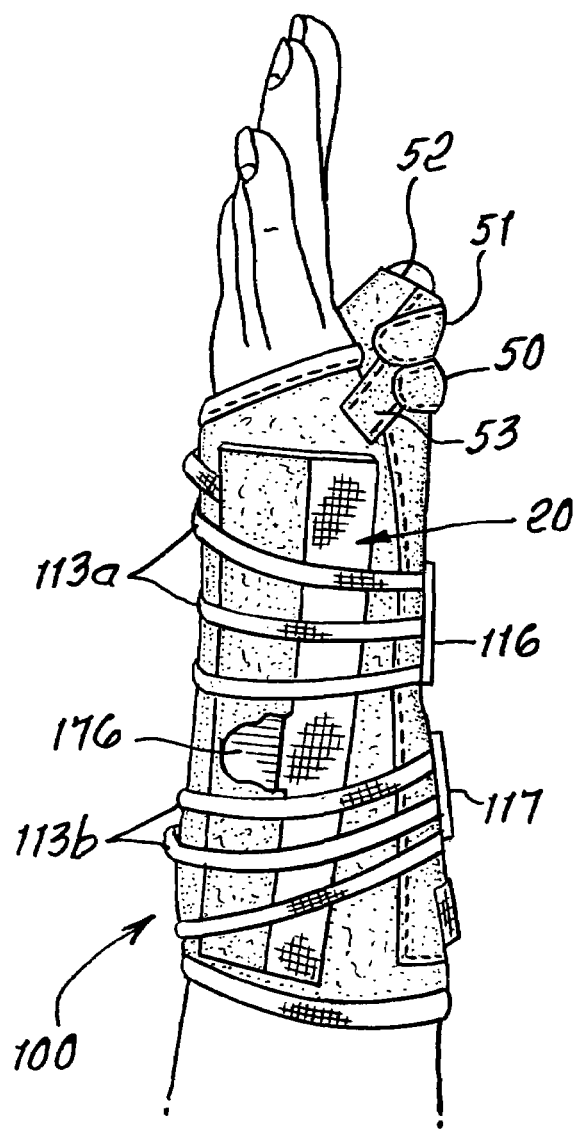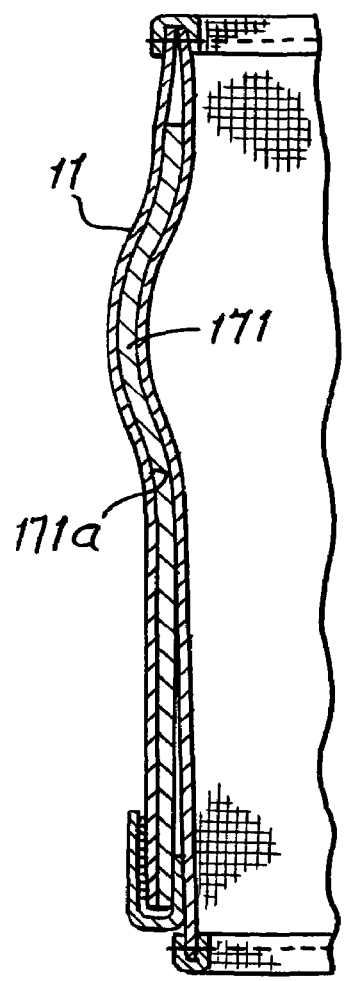

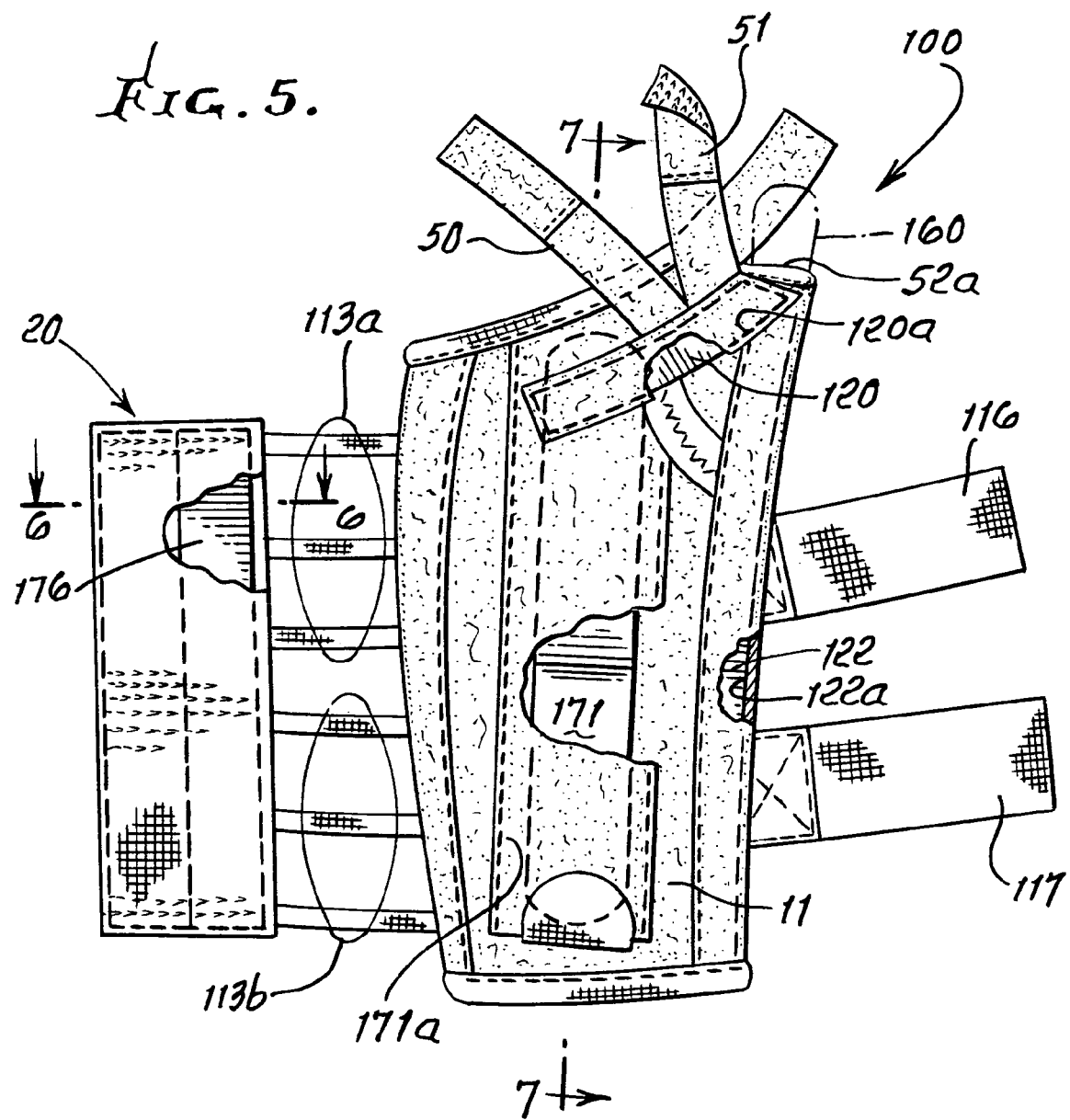
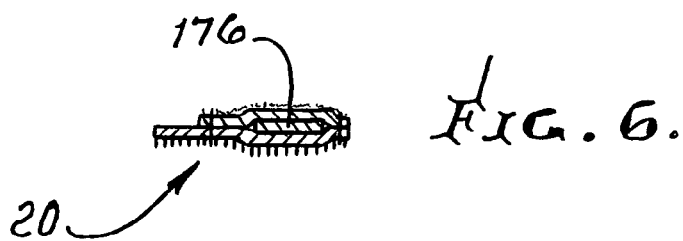

THUMB BRACE

BACKGROUND OF THE INVENTION

This invention relates generally to a brace operable to immobilize, or substantially immobilize, the thumb of the user; and more particularly concerns a brace applicable to the wrist of the user or wearer, for locating anchoring stays or stiffeners in positions adjacent to the user's thumb, and for enabling a tightening strap or straps to be wrapped relative to the thumb, and proximate to the multiple stiffeners.

Prior braces lacked the unusually advantageous combinations of features referred to, as well as the wide ranges of fit and adjustability, both about the wrist and also in immobilizing relation to the wearer's thumb. There is need for the multiple improvements in a brace as is now afforded by the present invention.

SUMMARY OF THE INVENTION

It is a major object of the invention to provide an improved brace construction and configuration, meeting the above needs. Basically, the improved device comprises:

a) a brace having multiple elongated stiffeners with extents generally alongside the thumb, b) and strap means carried to wrap relative to the thumb and proximate such stiffeners extents, c) whereby main extent of the thumb is substantially immobilized by the stiffeners and strap means, at least one stiffener extending to a wrist zone of the sleeve.

As will appear, the strap means typically include at least one resiliently stretchable, for example elasticized, strap which is tightenable about one or more of the stiffeners.

Another object is to provide two stretchable straps extensible from a junction or yoke prior to being stretched and wrapped proximate the stiffener extents. Three straps may preferably be provided to be tightenable relative to three stiffeners that extend to different terminal positions proximate multiple sides of the thumb; and two of those straps may be stretchable while the third is not. The stiffeners may be metallic and bent or curved to conform to wrist and thumb contours.

Yet another object is to provide a brace comprising a) an elongated brace body, adapted to be applied lengthwise of the thumb region of the hand, b) holder structure including flaps carried by the body and configured to be wrapped proximate at least one of the following:

i) hand,
 ii) fingers,
 iii) thumb, c) retention means on the brace to retain the holder structure in wrapped condition, relative to the body, d) at least one elongated stiffener carried by the body in position extending closely proximate the thumb and having configuration to hold the thumb in selected flexed condition, e) and means extending at an angle to the stiffener to assist the stiffener or stiffeners in holding the thumb in selected flexed condition.

As will be seen, multiple (two or three) of such stiffeners may be provided, and configured relative to the thumb to circumferentially immobilize the thumb as when multiple straps are wrapped in inward tightening relation to the stiffeners.

These and other objects and advantages of the invention, as well as the details of an illustrative embodiment, will be more fully understood from the following specification and drawings, in which:

DRAWING DESCRIPTION

FIG. 2 is a perspective view of the opposite side of the FIG. 1 brace, as applied to the palm side of the hand and thumb;

FIG. 3 is a side view taken on lines 3—3 of FIG. 2;

FIG. 5 is an elevation view of the brace, prior to wrapping of tightening means about the wrist;

FIG. 6 is a section taken on lines 6—6 of FIG. 5;

FIG. 7 is a section taken on lines 7—7 of FIG. 5;

DETAILED DESCRIPTION

Figure 8:
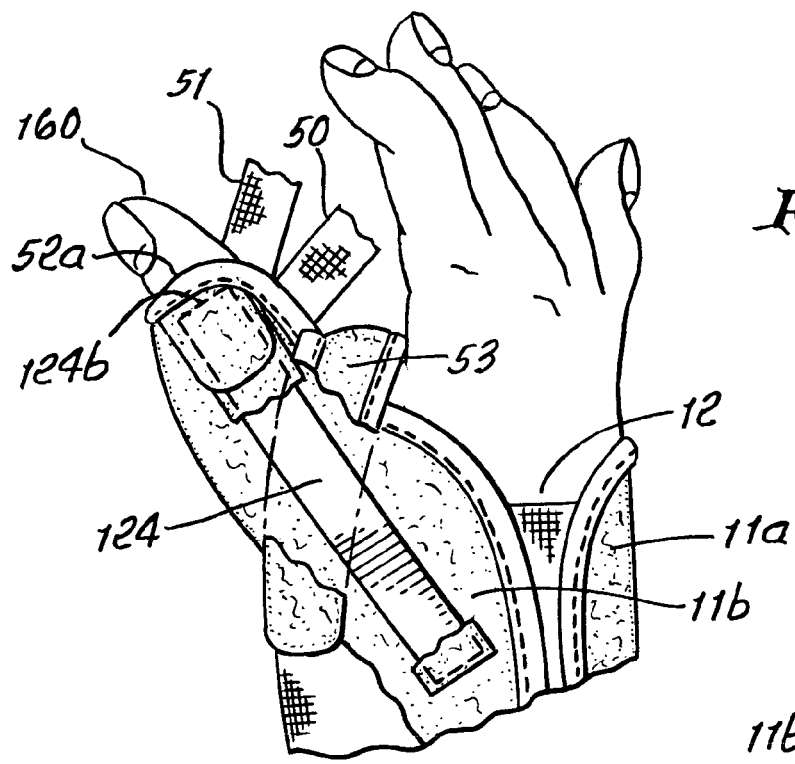
FIG. 8 is a view showing application of structure to the user's wrist and thumb, as viewed toward the back side of the wrist and thumb.

In the drawings, the preferred brace 100 includes an elongated flexible holder, in the form of a sleeve 11, sized to loosely receive the user's wearer's wrist 12, as in FIG. 8. The sleeve includes two flexible flaps, first flap 11a and second flap lib, adapted to be relatively closed toward sides of the wrist to secure the holder sleeve about the wrist.

Figure 4:
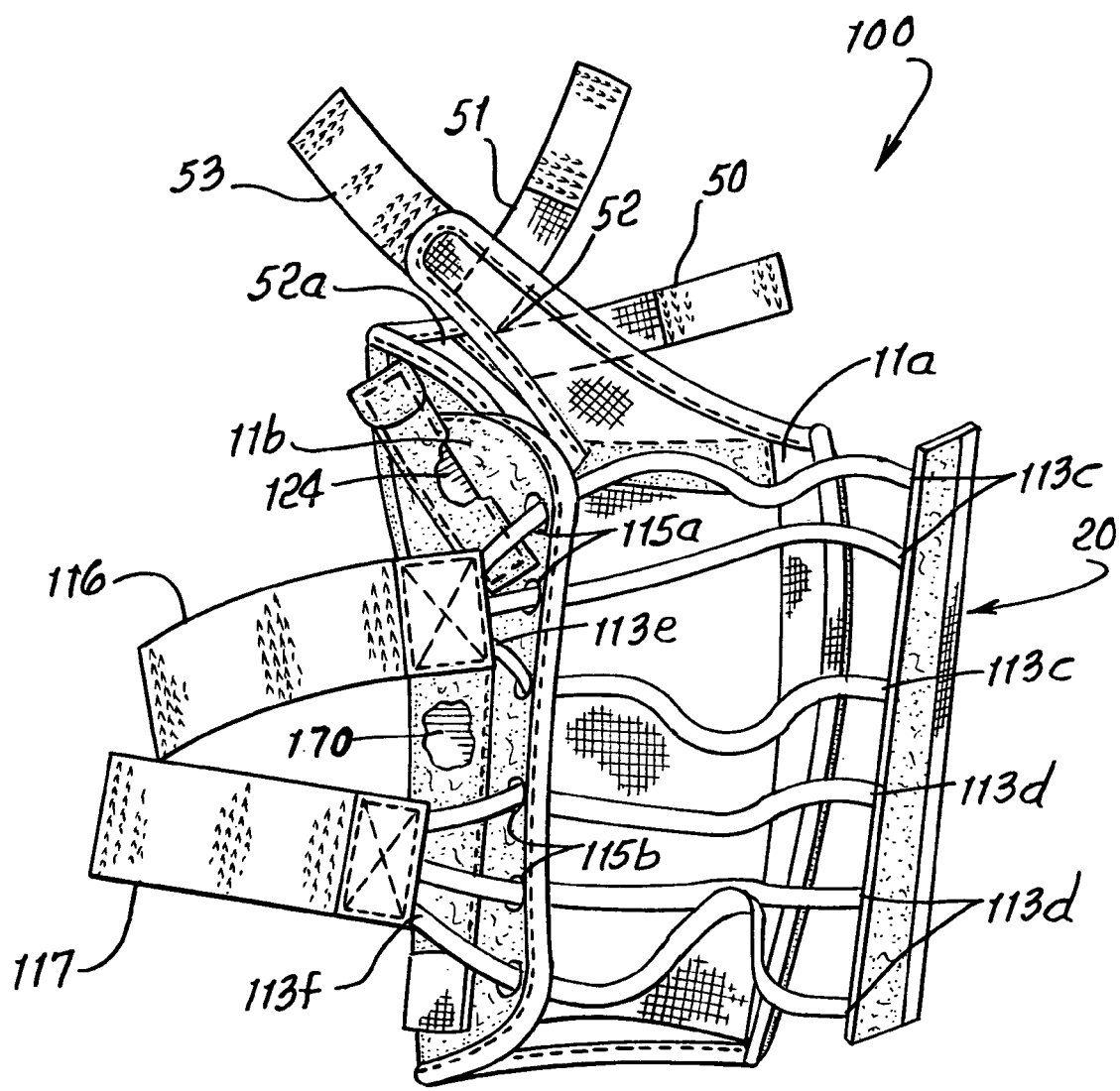
FIG. 4 is a plan view of the brace in unwrapped, opened condition.

Tightening or tensioning laces or strands 13, configured in two groups 113a and 113b, see FIG. 5, are spaced along the length of the sleeve. Ends 113c of strands in group 113a are connected to a strand anchoring overflap 20, (see FIG. 4), adjustably attached as by VELCRO, to outer surface of flap 11a; and ends 113d of straps in group 113b are also attached to strand anchoring overflap 20. See FIG. 4. Overflap 20 can be adjusted in its position relative to flap 11a due to its VELCRO connection thereto.

Figure 1:
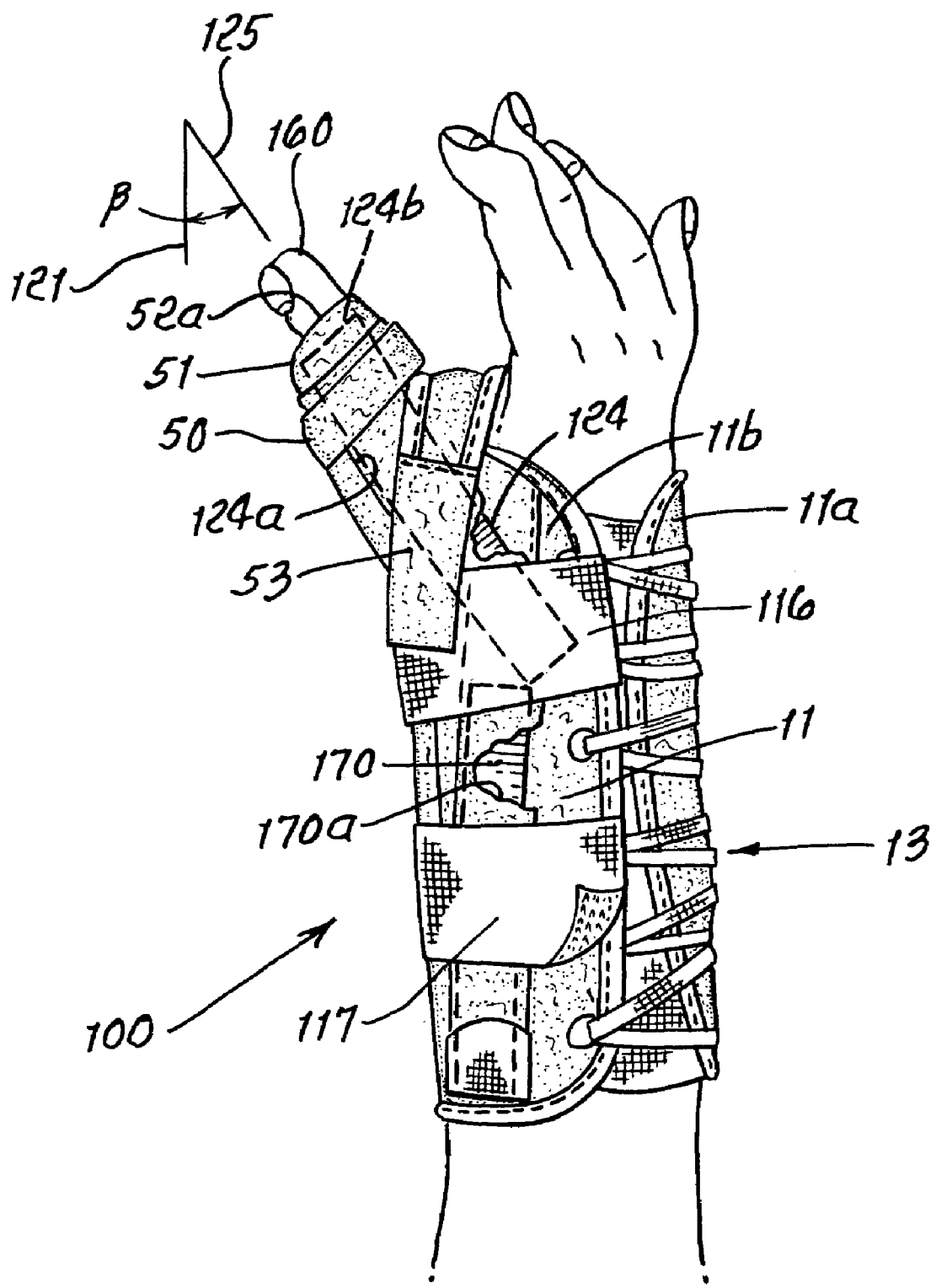
FIG. 1 is a perspective view of one side of the brace, applied to a user's right hand, and thumb.

Strands or laces in group 113a pass through eyelet openings 115a in flap lib; and strands or laces in group 113b pass through eyelet openings 115b in flap lib. Ends 113e of strands in group 113a are attached to a tightener 116, and ends 113f of strands in group 113b are attached to a tightener 117 spaced along the sleeve 11 from tightener 116. When the tighteners are pulled taut to tighten the strands about the flaps 11a and 11b, about the user's wrist, the tighteners can then be VELCRO attached to the outer surface of the flap lib, as seen in FIG. 1, and with optimum position adjustment on that outer surface, for optimum comfortable attachment to the wrist, with maximum security and bracing effect. These objectives are enhanced by grouping of the strands in two groups 113a and 113b, separately adjustable, along with separate position adjustability of the tighteners 116 and 117.

It is a feature of the invention that the user's thumb is, or can readily be, substantially immobilized by multiple elongated stiffeners having thumb positioning extents generally alongside, or proximate, different sizes of the thumb. See for, example, the following representative stiffeners:

stiffener 120 extending in pocket 120a in FIG. 2 and at an angle α (between 30° and 70°) relative to the longitudinal direction 121 of the sleeve 11 (see FIG. 2), and terminating at 120b alongside the thumb 160;

stiffener 122 extending generally in direction 121 in a pocket 122a and terminating upwardly at 122b, alongside the thumb and 120b, lower extent at the stiffener being anchored to the body, and overlapping by certain tightener strands 13, at wrist level, for anchoring the thumb in position, stiffener 124 extending in direction 125 in FIG. 1, at an angle β relative to direction 121, and in pocket 124b, and terminating upwardly at 124b alongside the thumb.

Figure 10:
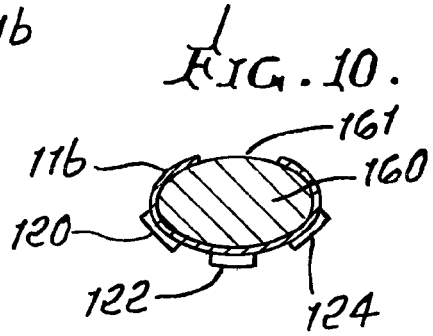
FIG. 10 is a cross section taken through the user's thumb at a position showing locating of three stiffeners adjacent different side portions of the thumb.

See also FIG. 10, taken in schematic section through the upper extent of flap 11b and through the thumb 160, near the thumb joint nearest the thumb nail, and showing the positions of the three stiffeners spaced about the thumb and at three thumb captivating positions and resisting thumb bending. The stiffeners may consist of thin metal strips, that resist bending. The stiffeners may be pre-bent to hold the thumb in slightly flexed, comfortable position, for long periods of time as the brace is worn. Two stiffeners could be provided, if they were sized and positioned in thumb captivating position, blocking thumb flexing, as with the assistance of retention straps carried to wrap relative to the thumb, proximate stiffeners extents, for immobilizing the thumb. Note strap closing of the flap gap 161 in FIG. 10. However, three circumferential point immobilizing stability as respects the main extent of the thumb, is provided by three stiffeners as described, is preferred.

As referred to, strap means is carried by the sleeve 11 to wrap relative to the thumb and proximate stiffener extents alongside the thumb, to assist in thumb immobilization, over periods of time as the brace is worn, as by strap tightening of the stiffeners adjacent the thumb, and thumb captivation by closing of the flap gap 161. The strap means typically includes at least one resiliently, lengthwise stretchable strap, and as provided by one or both of the straps 50 and 51 seen in FIG. 4. It will be seen that straps 50 and 51 diverge away from a junction 52, in that view, i.e. prior to stretching and wrapping of one or both of such straps, relatively about the end portions of the stiffeners carried in the body of the sleeve proximate the thumb opening 52a from the sleeve. Note also the provision of a third strap 53 extending crosswise of and angularly away from straps 50 and 51, in FIG. 4. See also FIG. 5. FIGS. 1–3 show the straps in wrapped positions, straps 50 and 51 having been resiliently stretched during wrapping, to firmly bind as by VELCRO attachment to the surface material on the sleeve, or carried on the sleeve, and provide binding tension, enhancing the desired immobilizing effect on the stiffeners and thumb. Looping strap 53 is wrapped over the web region between the thumb and forefinger, as best seen in FIG. 1, and has VELCRO attachment to the surface material on the sleeve and on the tightener 116, strap 53 overlapping stiffener 124.

Figure 9:
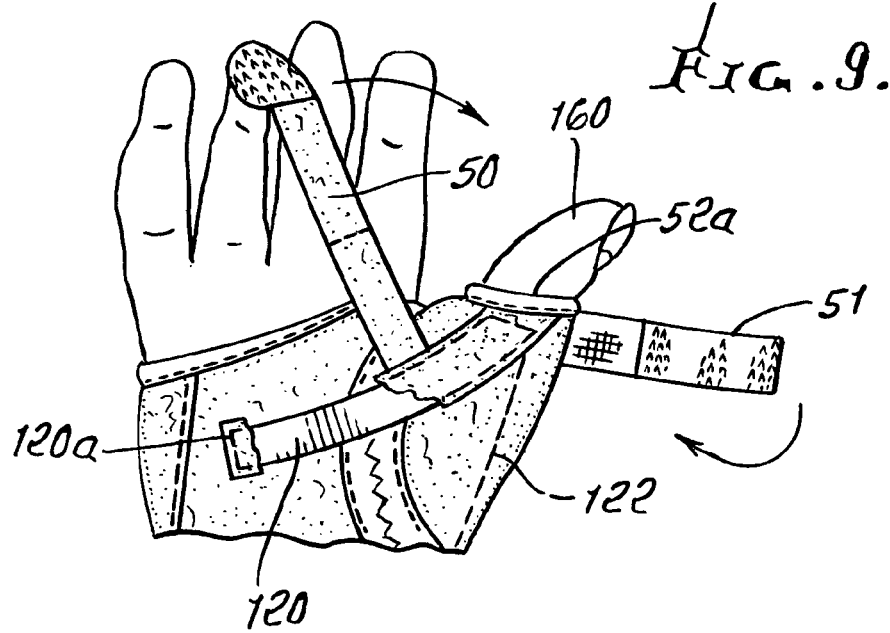
FIG. 9 is a view showing application of structure to the user's wrist and thumb, as viewed from the palm side of the wrist and thumb.

FIGS. 1 to 3 show straps 50 and 51 wound about the thumb zone and about sleeve material, and about stiffeners 120, 122 and 124. FIG. 8 shows straps 50 and 51 extended in position to be initially wrapped about the stiffener 124. In FIG. 9, strap 50 is extended as in FIG. 2, but strap 51 is in process of being wound so as to extend over angled stiffener 120.

Additional flap stiffeners are shown at 170 and 171, in pocket 170a and 171a, and elongated as shown, and to assist one or more of stiffeners 120, 122 and 124. See also stiffener 176 in over-flap 20.

What is claimed is:

1. A thumb and wrist brace comprising, in combination
   a) the brace having three elongated stiffeners with extents in pockets extending upwardly to terminals adjacent and generally alongside the thumb,
   b) and strap means carried to wrap relative to the thumb and proximate said stiffener extents,
   c) whereby the main extent of the thumb is substantially immobilized by the stiffeners and strap means,
   d) at least one of said stiffeners extending to a wrist zone of the brace,
   e) the brace having a body defining holder flaps which are tightened together to stabilize the brace on the user's wrist, said one stiffener anchored to the brace body proximate at least one of said flaps whereby the brace is stabilized against flexing between the thumb and wrist.

2. The combination of claim 1 wherein the strap means includes at least one resiliently stretchable strap.

3. The combination of claim 1 wherein the strap means includes at least two resiliently stretchable straps.

4. The combination of claim 3 wherein said two stretchable straps are extensible from a junction or yoke prior to being stretched and wrapped proximate said stiffener extents.

5. The combination of claim 3 wherein the strap means includes a third strap.

6. The combination of claim 1 wherein said stiffener extents have terminals alongside and spaced about the thumb.

7. The combination of claim 1 wherein said three elongated stiffeners extend generally alongside different portions of the thumb.

8. The combination of claim 7 wherein said stiffeners are metallic and at least two stiffeners being adjustably and selectively configured to conform to different wrist and thumb contours, there being a stiffener portion angled in spaced relation to the thumb, the strap means including a strap that wraps generally lengthwise over said angled portion.

9. The combination of claim 7 wherein the strap means includes at least two resiliently stretchable straps.

10. The combination of claim 9 wherein said two stretchable straps are extensible from a junction or yoke prior to being stretched and wrapped proximate said stiffener extents.

11. The combination of claim 9 wherein strap means includes a third strap.

12. The combination of claim 10 wherein the stiffener extents have terminals alongside the thumb.

13. The combination of claim 12 wherein said stiffeners are metallic and adjustable configured to conform to wrist and thumb contours.

14. The combination of claim 7 wherein said two stretchable straps are extensible from a junction or yoke prior to being stretched and wrapped proximate said stiffener extents.

15. The combination of claim 14 wherein the strap means includes a third strap.

16. A thumb brace, comprising
   a) an elongated brace body, adapted to be applied lengthwise of the thumb region of the hand,
   b) holder structure including flaps carried by the body and configured to be wrapped proximate at least one of the following:

i) hand,
ii) fingers,
iii) thumb,
c) retention means on the brace to retain the holder structure in wrapped condition, relative to the body,
d) three elongated stiffeners carried by the body in positions extending closely proximate the thumb and having configurations to hold the thumb in selected flexed condition, at least one stiffener being metallic and elongated to extend from thumb proximity to wrist proximity and anchored to the holder at said wrist proximity, to stabilize the brace against flexing between said thumb and wrist proximities,
e) and strap means extending at an angle to said stiffeners to assist the stiffeners in holding the thumb in selected flexed condition.

17. The brace of claim 16 wherein the holder structure includes multiple holders spaced apart lengthwise of said body, and extending generally transversely thereof.

18. The brace of claim 17 wherein the holders comprising bands.

19. The brace of claim 17 wherein the holders comprise strands, said one stiffener anchored to the brace body proximate at least one of said strands which extends about the wearer's wrist.

20. The brace of claim 16 wherein there are at least two stiffeners that extend proximate the thumb knuckle closest to the tip of the thumb.

21. The brace of claim 20 wherein said three stiffeners are configured relative to the thumb to circumferentially immobilize the thumb against lateral bending.

22. The brace of claim 16 wherein the brace body defines a tubular portion in which the thumb extends, the stiffener or stiffeners extending adjacent a wall formed by said tubular portion.

23. The brace of claim 16 wherein the body defines an elongated sleeve carrying said stiffeners and strap means, the sleeve sized to fit about the user's wrist, and tightening means including multiple strands adjustably carried by the sleeve.

24. The brace of claim 23 wherein the strands are in two groups, spaced along the sleeve length, there being two tighteners respectively associated with the two groups of strands.

25. The brace of claim 24 wherein stiffeners carried by the sleeve are overlapped by strands.

26. The brace of claim 17 wherein said holder structure includes an over-flap connected to said multiple holders in the form of strands, there being an auxiliary stiffener carried by said over-flap and extending cross-wise of the directions of at least certain of the strands.

* * * * *